United States Patent
Suddaby

(10) Patent No.: US 6,875,173 B2
(45) Date of Patent: Apr. 5, 2005

(54) LAMINECTOMY SUCTION AND RETRACTION DEVICE

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 147 days.

(21) Appl. No.: 10/346,180

(22) Filed: Jan. 17, 2003

(65) Prior Publication Data

US 2004/0143164 A1 Jul. 22, 2004

(51) Int. Cl.[7] .................................................. A61B 1/32
(52) U.S. Cl. ....................................................... 600/210
(58) Field of Search ................................ 600/184, 201, 600/204, 206, 208, 210, 217

(56) References Cited

U.S. PATENT DOCUMENTS

| | | | |
|---|---|---|---|
| 1,613,373 A | * | 1/1927 | Beck .......................... 600/205 |
| 1,930,712 A | * | 10/1933 | Girvin ......................... 433/93 |
| 2,255,657 A | * | 9/1941 | Hyman ........................ 433/29 |
| 4,049,000 A | | 9/1977 | Williams |
| 4,058,896 A | | 11/1977 | Moore |
| 4,068,664 A | | 1/1978 | Sharp et al. |
| 4,883,426 A | | 11/1989 | Ferrer |
| 5,123,403 A | | 6/1992 | Lavyne |
| 5,123,840 A | | 6/1992 | Nates |
| 5,287,848 A | * | 2/1994 | Cubb et al. ............. 128/200.26 |
| 5,690,660 A | | 11/1997 | Kauker et al. |
| 5,755,660 A | * | 5/1998 | Tyagi ........................ 600/205 |
| 5,803,904 A | | 9/1998 | Mehdizadeh |
| 5,891,018 A | * | 4/1999 | Wells ......................... 600/226 |
| 5,961,522 A | | 10/1999 | Mehdizadeh |
| 6,001,077 A | | 12/1999 | Ellman et al. |
| 6,210,323 B1 | | 4/2001 | Gilhuly et al. |
| 6,241,658 B1 | * | 6/2001 | Goodrich .................... 600/210 |
| 6,312,447 B1 | | 11/2001 | Grimes |
| 2003/0060685 A1 | * | 3/2003 | Houser et al. .............. 600/206 |

* cited by examiner

Primary Examiner—Eduardo C. Robert
Assistant Examiner—Anuradha Ramana
(74) Attorney, Agent, or Firm—Shoemaker and Mattare

(57) ABSTRACT

A laminectomy suction and retraction device has a body with an offset probe extending therefrom. The tip of the probe has a retraction blade having a pair of suction ports lying above a pair of ports in the distal end surface of the probe. A rectangular port is formed by the end surface of the probe, adjacent the blade surface.

12 Claims, 3 Drawing Sheets

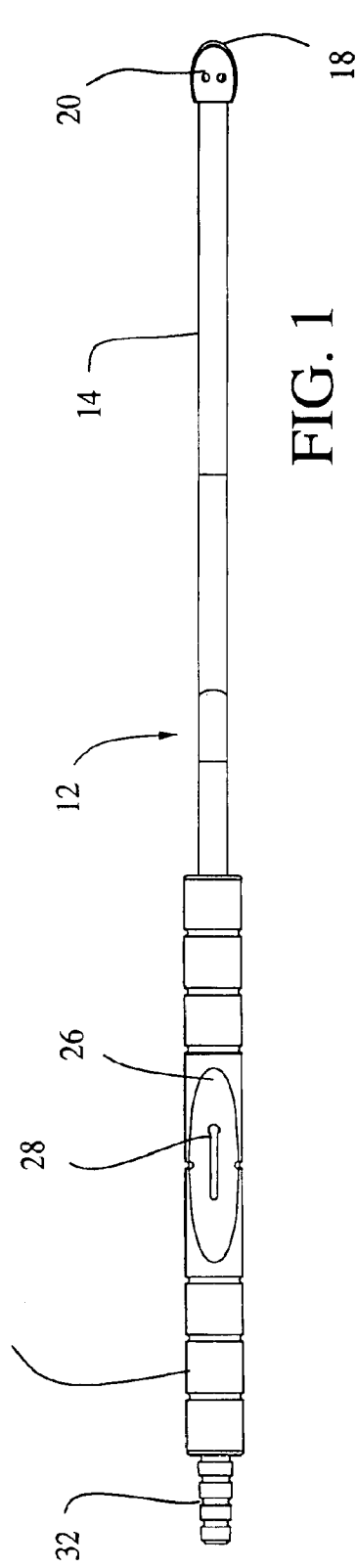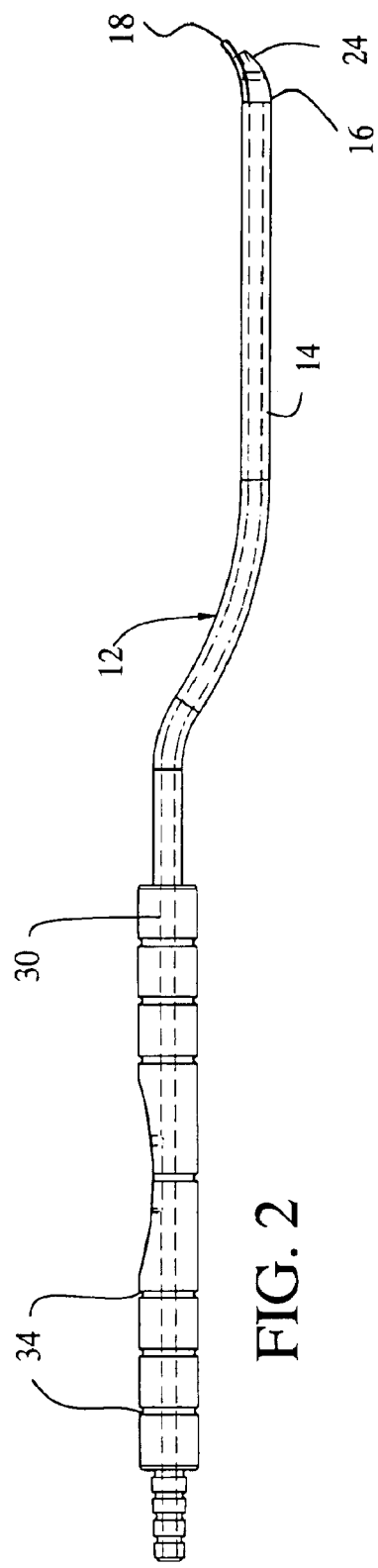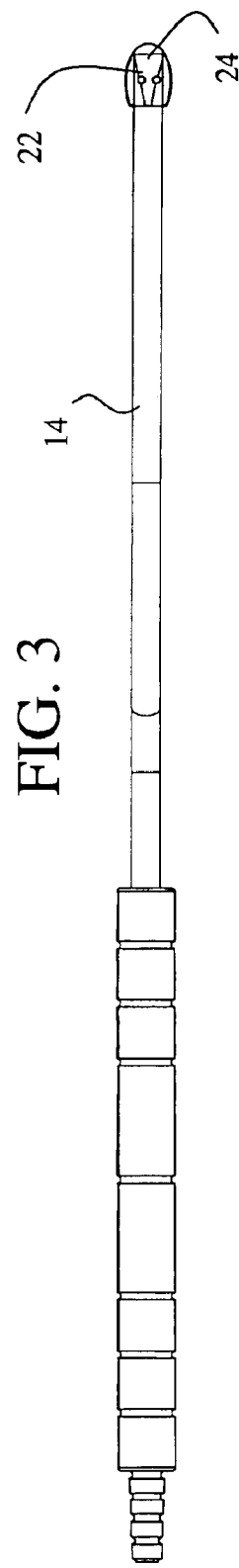

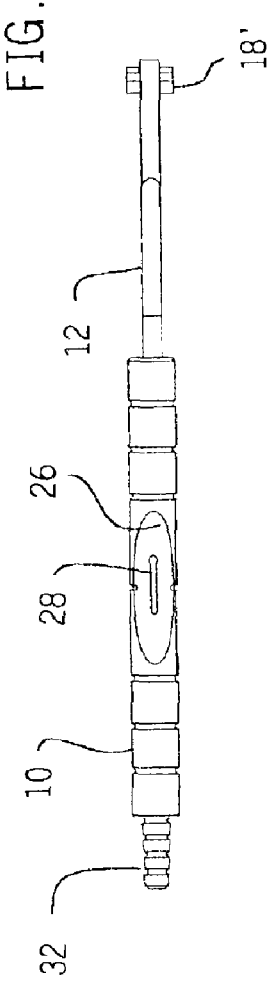
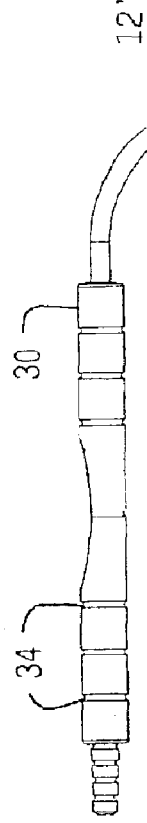
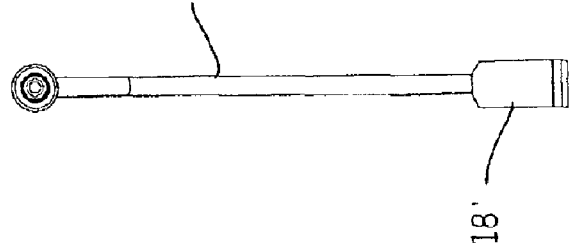
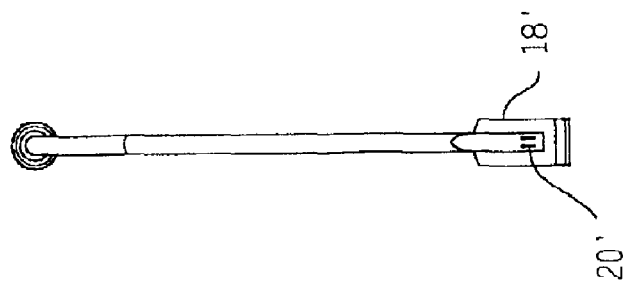

LAMINECTOMY SUCTION AND RETRACTION DEVICE

BACKGROUND OF THE INVENTION

This invention relates to a laminectomy suction and retraction device.

Prior inventors have patented a number of surgical suction probes having, typically, a handle with a probe extending therefrom, and means such as a hole in the side of the body for controlling application of suction to the tip of the probe. Some probes have spatula-like retractor blades adjacent the suction orifice to enable the surgeon to retract nerves or vessels while removing fluids from the incision. Representative prior includes U.S. Pat. Nos. 4,058,896, 4,883,426, 5,123,840, 5,961,522, 6,312,447, 4,049,000, 4,068,664, 5,123,403, 5,690,660, 5,803,904, 6,001,077, 6,087,587 and 6,210,323. Such devices are prone to clogging, and do not prevent the surgeon from traumatizing tissues by inadvertently applying too much force to the retraction tool.

SUMMARY OF THE INVENTION

An object of the invention is to improve the retraction function of a surgical suction tool.

These and other objects are attained by a laminectomy suction and retraction device as described below.

The present device provides multiple suction apertures or ports at the tip to permit suction to continue even when one of the ports is clogged.

BRIEF DESCRIPTION OF THE DRAWINGS

In the accompanying drawings,

FIG. 1 is a top plan view of a laminectomy suction and retraction device embodying the invention;

FIG. 2 is a front elevation thereof;

FIG. 3 is a bottom plan view thereof;

FIG. 6 is a top plan view of a second embodiment of the invention;

FIG. 7 is a front elevation thereof,

FIG. 8 is a bottom plan view thereof,

FIG. 9 is a right side elevation thereof; and

FIG. 10 is a left side elevation thereof

DESCRIPTION OF THE PREFERRED EMBODIMENT

Figure 5:
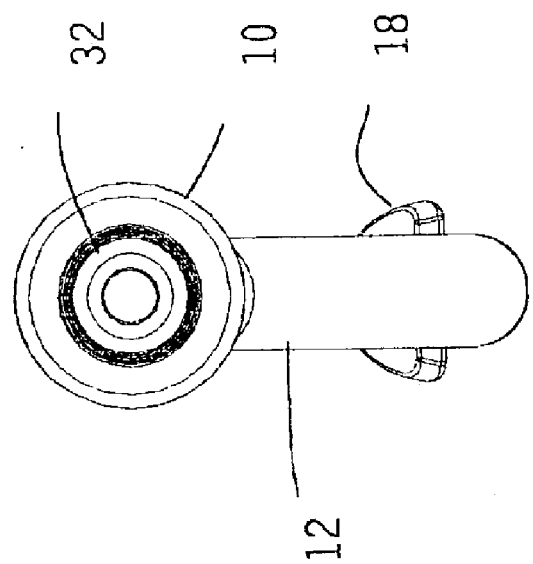
FIG. 5 is a left side elevation thereof

A laminectomy suction and retraction device embodying the invention has a body 10 (FIG. 1) with a probe 12 extending therefrom. The probe has a straight segment 14 which is parallel to but offset from the longitudinal axis of the body. The tip 16 of the probe has a duckbill-like spatula blade 18 which has a upper pair of suction ports 20 lying above a lower pair of ports 22 in the distal end surface 24 of the probe. The end surface 24 is angulated so that an imaginary line perpendicular to its surface makes an angle of about 45° to the axis of the straight portion. The end surface 24 defines a large rectangular suction port 25 at its distal termination. Thus, in all, there are five suction ports: the pair of ports 20, the ports 22, and the rectangular port 25.

The body has a depression 26 (FIG. 1) with a slot 28 at its bottom communicating with the air passage 30 which extends lengthwise through the body. A fitting 32 is provided at the proximal end of the body for a suction hose, not shown. The spaced annular grooves 34 on the body improve gripping.

In use, the tool is connected to a source of suction, and the surgeon positions the tool within the incision. When he desires to apply suction, he covers the slot 28 with a finger. The tool may be manipulated simultaneously to depress dura or to retract nerve root sleeves while providing adequate suction of blood or fluid to provide clear visualization. Alternatively, the spatula blade 18 may be manipulated as a dissection tool to allow separation of spinal dura matter from the lateral spinal canal in situations where the dura has become excessively adherent.

Figure 4:
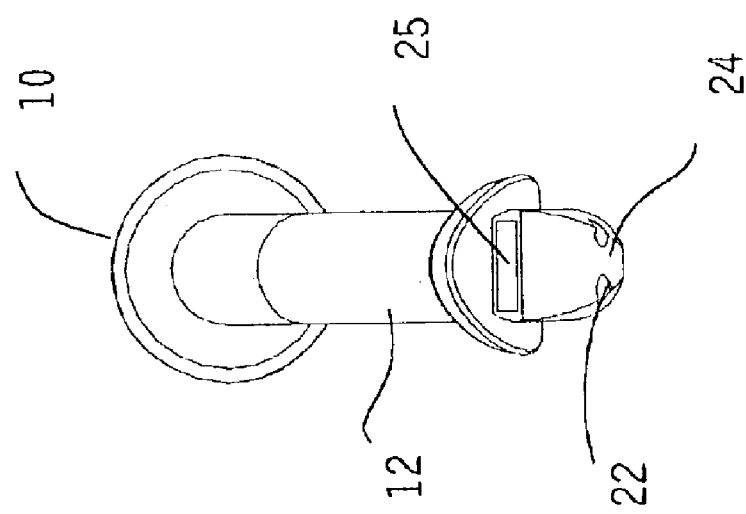
FIG. 4 is a right side elevation thereof.

The tool shown in FIGS. 6–10 is identical to that shown in FIGS. 1–5, except for the probe 12'. Here, the elbow 13' is configured so that the straight portion 14' of the probe extends steeply downward from the body, at an angle of about 75° from the axis body. The tip also has a blade 18', but of a different shape from that of the first embodiment. The tip 16' is bent slightly downward from the straight portion of the probe, so that the tip extends substantially perpendicular to the axis of the body. The blade is affixed to the proximal surface of the tip, and its lower end 17' is bent back 90°, so that is parallel to the body axis. This construction enables to the surgeon to hook a nerve with the end 17', to keep it out of the way during the procedure. In this embodiment, there are only two suction ports, i.e., the holes 20 in the distal surface of the blade, the holes 22, and the rectangular aperture 25. All of these ports communicate with the vacuum source via the hollow probe stem.

Particularly in the second embodiment of the invention, I prefer the probe be substantially flexible. This is done by making the probe of a low-modulus material such as a plastic or elastomeric material, and then selecting the dimensions of the probe shaft so that it will flex substantially under a tip load of about 75 grams or more. If the surgeon displaces the tool too much, creating a danger of exceeding this limit, the shaft flexes and gives way gradually and in a controlled fashion to prevent over-retraction. The large offset of the second embodiment produces a greater bending moment in the shaft for a given tip force, than in the first embodiment. For the second embodiment, I prefer that the shaft be designed so that the elbow 13' bends about 10° for each 2 grams of force over 75 grams, but the degree of flexibility will depend on the procedure and may be a personal preference of the surgeon.

Since the invention is subject to modifications and variations, it is intended that the foregoing description and the accompanying drawings shall be interpreted as only illustrative of the invention defined by the following claims.

I claim:

1. A laminectomy suction and retraction device comprising
   a hollow elongate body having an air passage extending from a proximal end of the body to the a distal end of the body,
   a fitting at the proximal end of the body for connection to suction tubing,
   a hollow probe extending forward from the distal end of the body, said probe having a tip with a distal end surface inclined at an angle to the longitudinal axis of the probe, and a blade having a width greater than a width of said distal end surface and a length such that part of the blade extends beyond said end surface,
   said blade having a pair of suction ports in its distal end surface.

2. The device of claim 1, wherein said tip has a pair of suction ports in its distal end surface.

3. The device of claim 1, wherein the distal end surface of the probe defines a rectangular suction port.

4. The device of claim 1, wherein the probe is configured so that the tip is offset from the longitudinal axis of the body, the blade being closer to said axis than the distal end surface of the probe.

5. The device of claim 1, further comprising at least one lateral hole on the body, which a surgeon can cover with a finger to control delivery of suction to the tip of the tool.

6. The device of claim 1, wherein a portion of the probe adjacent the tip is straight.

7. The device of claim 6, wherein the straight portion extends along an axis parallel to but offset from the longitudinal axis of the body.

8. The device of claim 6, wherein the straight portion extends along an axis which makes a substantial angle to the longitudinal axis of the body.

9. The device of claim 8, wherein said angle is about 75°.

10. The device of claim 8, wherein the distal tip of the probe is bent downward from the straight portion so that it is about perpendicular to the axis of the body.

11. The device of claim 10, further comprising a retraction blade affixed to the tip, said blade having a distal portion which is bent rearwardly about 90° so that it is substantially parallel to the axis of the body.

12. The device of claim 8, wherein the probe is made of a flexible plastic.

* * * * *